United States Patent
Shigemori et al.

(10) Patent No.: US 7,880,765 B2
(45) Date of Patent: Feb. 1, 2011

(54) RECEIVING APPARATUS

(75) Inventors: Toshiaki Shigemori, Hachioji (JP);
Seiichiro Kimoto, Hachioji (JP);
Manabu Fujita, Hino (JP); Ayako Nagase, Hachioji (JP); Akira Matsui, Hino (JP); Kazutaka Nakatsuchi, Hino (JP)

(73) Assignee: Olympus Corporation, Tokyo (JP)

( * ) Notice: Subject to any disclaimer, the term of this patent is extended or adjusted under 35 U.S.C. 154(b) by 1140 days.

(21) Appl. No.: 11/583,556

(22) Filed: Oct. 19, 2006

(65) Prior Publication Data

US 2007/0058036 A1    Mar. 15, 2007

Related U.S. Application Data

(63) Continuation of application No. PCT/JP2005/005866, filed on Mar. 29, 2005.

(30) Foreign Application Priority Data

Apr. 19, 2004    (JP)    ............... 2004-122653

(51) Int. Cl.
*H04N 9/47* (2006.01)
*H04N 7/18* (2006.01)

(52) U.S. Cl. ..................................... 348/77

(58) Field of Classification Search .............. None
See application file for complete search history.

(56) References Cited

U.S. PATENT DOCUMENTS

| | | | |
|---|---|---|---|
| 6,695,772 B1 * | 2/2004 | Bon et al. | 600/114 |
| 7,061,523 B2 * | 6/2006 | Fujita et al. | 348/77 |
| 2002/0109863 A1 * | 8/2002 | Monroe | 358/400 |
| 2002/0173718 A1 | 11/2002 | Frisch et al. | |
| 2003/0043263 A1 | 3/2003 | Glukhovsky et al. | |
| 2003/0085994 A1 | 5/2003 | Fujita et al. | |
| 2003/0213495 A1 | 11/2003 | Fujita et al. | |
| 2005/0049461 A1 * | 3/2005 | Honda et al. | 600/160 |

FOREIGN PATENT DOCUMENTS

| | | |
|---|---|---|
| DE | 195 29 367 A1 | 2/1997 |
| JP | 2001-245844 | 9/2001 |
| JP | 2003-19111 | 1/2003 |

(Continued)

OTHER PUBLICATIONS

Supplementary European Search Report dated Jun. 3, 2010.

(Continued)

*Primary Examiner*—Nhon T Diep
(74) *Attorney, Agent, or Firm*—Scully, Scott, Murphy & Presser, P.C.

(57) ABSTRACT

A receiving apparatus includes a receiving unit that receives an image signal, identification information on a transmitting apparatus, and color adjusting information that are radio transmitted from the transmitting apparatus; a lock controller that locks the color adjusting information when the receiving unit receives at least one of consecutively repeated identical color adjusting information and consecutively repeated identical identification information during a predetermined period or when the receiving unit most often receives at least one of the identical color adjusting information or the identical identification information during the predetermined period; and an image processing unit that performs image processing on the received image signal based on the locked color adjusting information.

3 Claims, 5 Drawing Sheets

FOREIGN PATENT DOCUMENTS

| | | |
|---|---|---|
| JP | 2003-523795 A | 8/2003 |
| JP | 2003-325439 | 11/2003 |
| JP | 2005-124961 | 5/2005 |
| WO | WO 01-35813 A | 5/2001 |

OTHER PUBLICATIONS

English language abstract of Japanese Patent Application Publication No. 2003-325439 published Nov. 18, 2003.
English language abstract of Japanese Patent Application Publication No. 2003-019111 published Jan. 21, 2003.

* cited by examiner

RECEIVING APPARATUS

CROSS-REFERENCE TO RELATED APPLICATIONS

This application is a continuation of PCT international application Ser. No. PCT/JP2005/005866 filed Mar. 29, 2005 which designates the United States, incorporated herein by reference, and which claims the benefit of priority from Japanese Patent Application No. 2004-122653, filed Apr. 19, 2004, incorporated herein by reference.

BACKGROUND OF THE INVENTION

1. Field of the Invention

The present invention relates to a receiving apparatus that receives radio image signals transmitted from a body-insertable apparatus, such as a swallowable capsule endoscope, inserted into a subject body by employing plural antennas arranged outside of the subject body. More particularly, the present invention relates to the receiving apparatus that performs image processing on the received radio image signals.

2. Description of the Related Art

In recent years, a capsule endoscope having an imaging function and a radio communication function makes an appearance in a field of endoscope. The capsule endoscope is swallowed from a mouth of a patient, i.e., the subject body for an observation (examination), and is eventually discharged naturally from a living body (human body) of the patient. While the capsule endoscope is inside the subject body, i.e., during an observation period, the capsule endoscope travels through organs (through body cavity) such as a stomach and a small intestine while following peristaltic motion of the organs, and the capsule endoscope sequentially images inside the organs by using the imaging function.

Further, during the observation period, i.e., while the capsule endoscope travels through the organs, image data obtained inside the body cavity by the capsule endoscope are sequentially transmitted outside of the subject body by the radio communication function such as Bluetooth, and stored in a memory that is provided inside an external receiving apparatus. When the patient carries around the receiving apparatus that has the radio communication function and a memory function, the patient can freely move without any inconveniences even during the observation period, i.e., after swallowing the capsule endoscope until discharging the capsule endoscope. After the observation, a doctor or a nurse can display an image inside the body cavity on a display unit such as a display based on the image data stored in the memory of the receiving apparatus to make a diagnosis.

In general, the receiving apparatus includes plural antennas dispersively arranged outside of the subject body to receive image signals transmitted from the capsule endoscope, and switchably selects one antenna that has small error in receiving the image signals to receive the image signals, and performs image processing on the received image signals. In a medical apparatus proposed in Japanese Patent Application Laid-Open No. 2003-325439, a capsule ID corresponding to a unique number such as a capsule serial number is superposed on image signals of the capsule, and externally transmitted in a frame format, so that a capsule-side switch for identifier setting is not necessary and an amount of information of the identifier is reduced.

SUMMARY OF THE INVENTION

A receiving apparatus according to one aspect of the present invention receives an image signal radio transmitted from a movable transmitting apparatus, and includes a receiving unit that receives identification information on the transmitting apparatus and color adjusting information that are radio transmitted from the transmitting apparatus with the image signal; a lock controller that locks the color adjusting information when the receiving unit receives at least one of consecutively repeated identical color adjusting information and consecutively repeated identical identification information during a predetermined period or when the receiving unit most often receives at least one of the identical color adjusting information or the identical identification information during the predetermined period; and an image processing unit that performs image processing on the received image signal based on the locked color adjusting information.

A receiving apparatus according to another aspect of the present invention receives an image signal radio transmitted from a movable transmitting apparatus, and includes a receiving unit that receives color adjusting information that is radio transmitted from the transmitting apparatus with the image signal; a lock controller that locks the color adjusting information when the receiving unit receives consecutively repeated identical color adjusting information during a predetermined period or when the receiving unit most often receives identical color adjusting information during the predetermined period; and an image processing unit that performs image processing on the received image signal based on the locked color adjusting information.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Exemplary embodiments of a receiving apparatus according to the present invention are explained in detail below with reference to FIGS. 1 to 5. The present invention, however, is not limited to the embodiments, and various modifications may be made without departing from the general inventive concept of the present invention.

Figure 1:
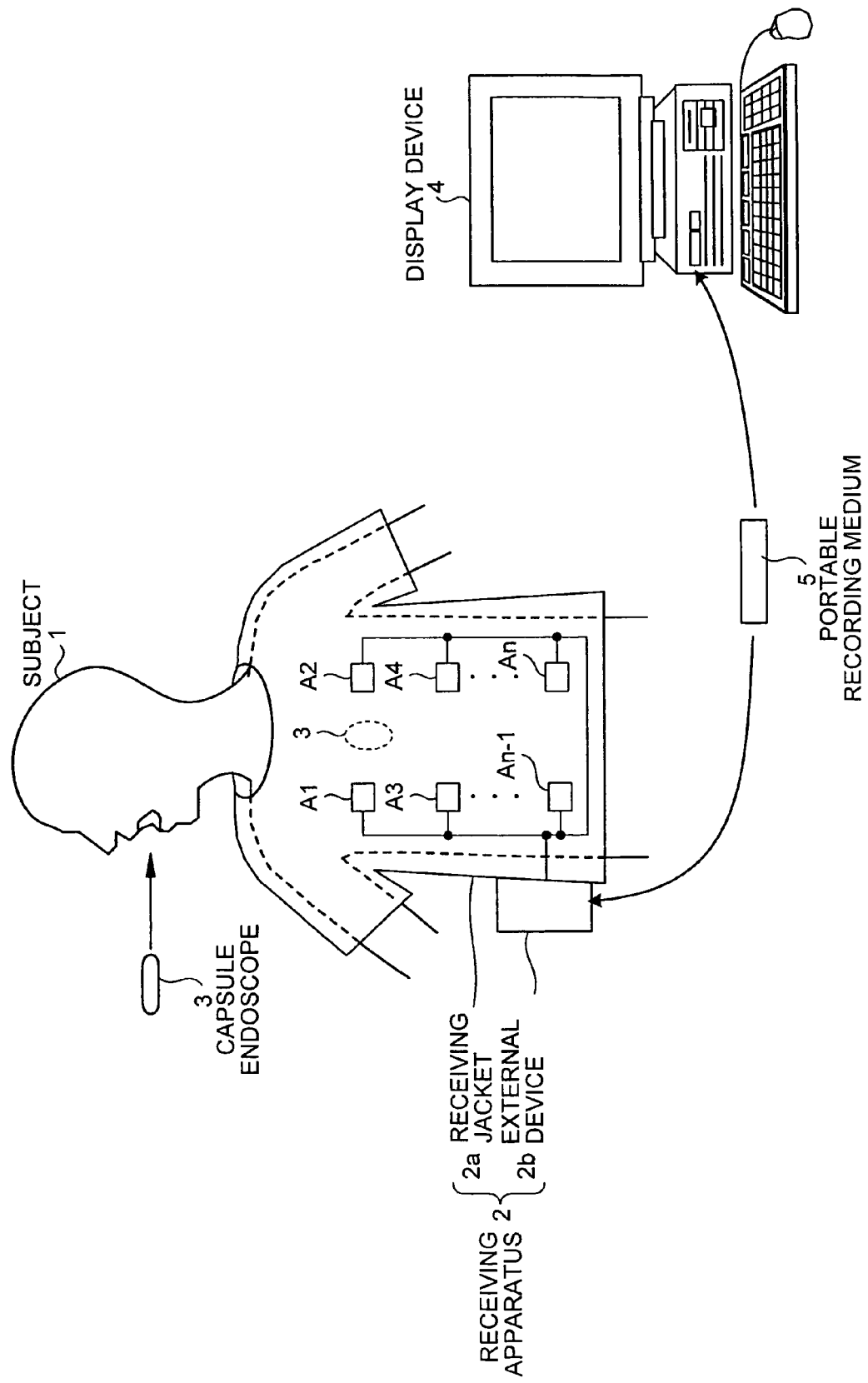
FIG. 1 is a schematic drawing showing an overall configuration of a wireless intra-subject information acquiring system having a receiving apparatus according to a first embodiment.

FIG. 1 is a schematic drawing showing an overall configuration of a wireless intra-subject information acquiring system having a receiving apparatus according to a first embodiment. In FIG. 1, the wireless intra-subject information, acquiring system has a receiving apparatus 2 and a capsule endoscope (body-insertable apparatus) 3. The receiving apparatus 2 has a radio receiving function. The capsule endoscope 3 is inserted into a subject 1, images inside a body cavity, and transmits data such as image signals to the receiving apparatus 2. Further, the wireless intra-subject information acquiring system has a display device 4 and a portable recording medium 5. The display device 4 displays an image inside the body cavity based on the image signals received by the receiving apparatus 2, and the portable recording medium 5 transfers data between the receiving apparatus 2 and the display device 4. The receiving apparatus 2 has a receiving jacket 2a that is worn by the subject 1 and an external device 2b that, for example, processes received radio signals.

The display device 4 displays the image inside the body cavity that is imaged by the capsule endoscope 3, and the display device 4 has a configuration such as a workstation that displays the image based on data acquired from the portable recording medium 5. More particularly, the display device 4 may have a configuration in which the image is directly displayed by a CRT display, a liquid crystal display, and the like, or a configuration in which the image is output to other medium such as a printer.

The portable recording medium 5 is detachable with respect to the external device 2b and the display device 4, and the portable recording medium 5 is capable of outputting and recording information when the portable recording medium 5 is attached to the external device 2b or the display device 4. In the present embodiment, the portable recording medium 5 is attached to the external device 2b and records the data transmitted from the capsule endoscope 3 when the capsule endoscope 3 travels through the body cavity of the subject 1. When the capsule endoscope 3 is discharged from the subject 1, i.e., when the imaging inside the subject 1 is finished, the portable recording medium 5 is removed from the external device 2b, and attached to the display device 4, and the data that are recorded in the portable recording medium 5 are read by the display device 4. The data can be transferred between the external device 2b and the display device 4 through, for example, the portable recording medium 5 that has a CompactFlash® memory and the like. Consequently, while imaging inside the body cavity, the subject 1 can move freely compared to when the external device 2b and the display device 4, are directly connected to each other through a cable. In the present embodiment, the portable recording medium 5 is employed to transfer the data between the external device 2b and the display device 4; however, the present invention is not limited thereto. For example, other built-in type recording apparatus such as a hard disk may be provided to the external device 2b. Then, the external device 2b and the display device 4 may be connected to each other through a cable or by radio to transfer the data therebetween.

Figure 2:
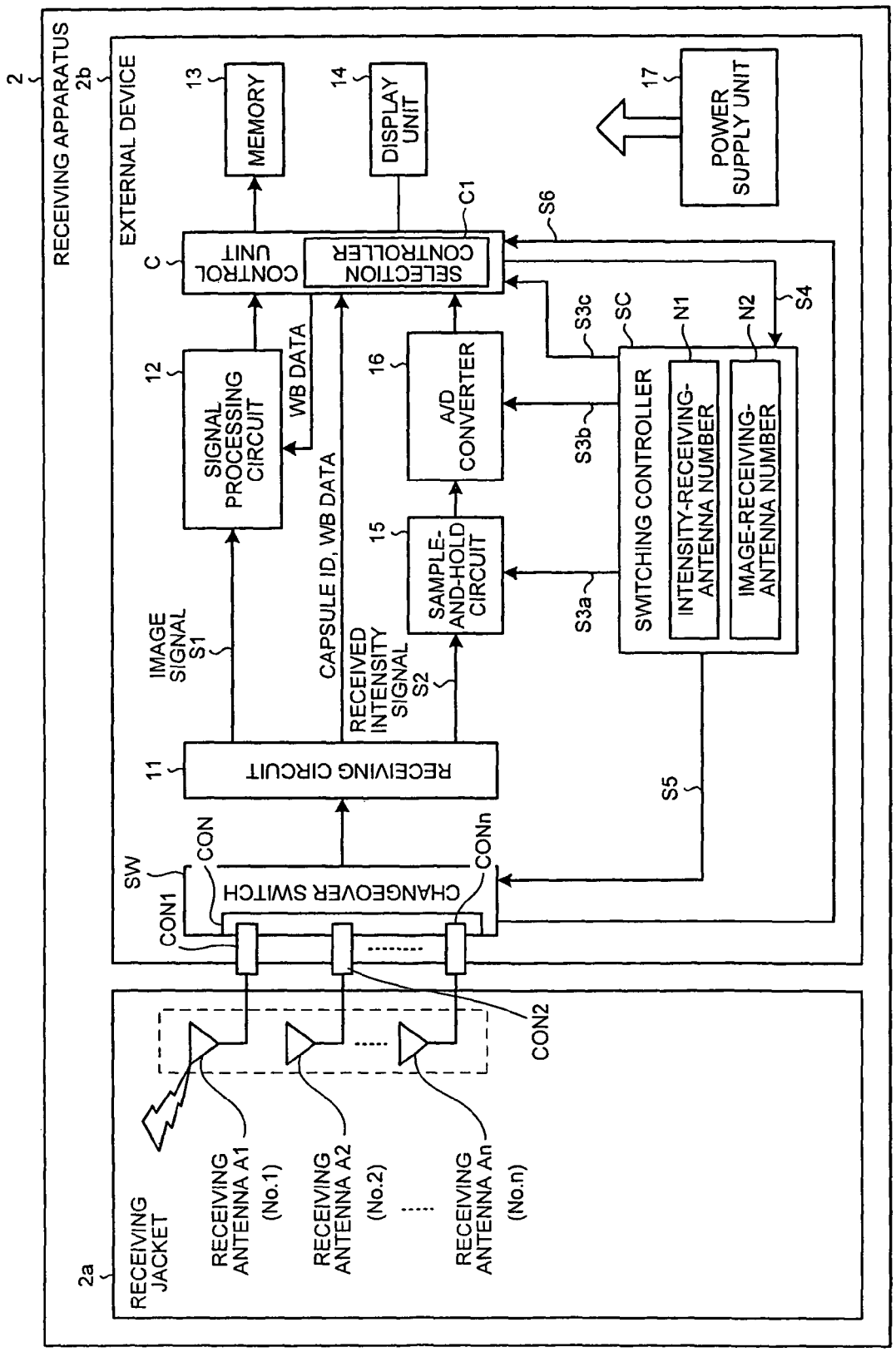
FIG. 2 is a block diagram showing a configuration of the receiving apparatus shown in FIG. 1.

Next, a configuration of the receiving apparatus is explained with reference to a block diagram of FIG. 2. The receiving apparatus 2 has a function of receiving the image data, which is radio transmitted from the capsule endoscope 3, inside the body cavity. As shown in FIG. 2, the receiving apparatus 2 has a shape wearable by the subject 1. Further, the receiving apparatus 2 includes the receiving jacket 2a that has receiving antennas A1 to An, and the external device 2b that, for example, processes radio signals received through the receiving jacket 2a. Each of the receiving antennas A1 to An may be attached directly to a body surface of the subject 1, rather than provided on the receiving jacket 2a. Alternatively each of the receiving antennas A1 to An may be detachably provided on the receiving jacket 2a.

The external device 2b has a function of processing the radio signals transmitted from the capsule endoscope 3. More particularly, as shown in FIG. 2, the external device 2b has a changeover switch SW and a receiving circuit 11. The changeover switch SW switches connections of each of the receiving antennas A1 to An. The receiving circuit 11 is connected to a subsequent stage of the changeover switch SW, and the receiving circuit 11 amplifies and modulates the radio signals sent from the receiving antennas A1 to An that are switched and connected by the changeover switch SW. Further, a signal processing circuit 12 and a sample-and-hold circuit 15 are connected to an output port of the receiving circuit 11. Furthermore, an A/D conversion unit 16 is connected to an output port of the sample-and-hold circuit 15.

A control unit C has a selection controller C1, which is a control means. The signal processing circuit 12, the A/D converter 16, a memory 13 that corresponds to the portable recording medium 5, a display unit 14, and a switching controller SC are connected to the control unit C. The switching controller SC has an intensity-receiving-antenna number N1 and an image-receiving-antenna number N2. The switching controller SC gives switching instructions to the changeover switch SW and gives processing timing instructions to the sample-and-hold circuit 15, the A/D converter 16, and the selection controller C1, based on the intensity-receiving-antenna number N1 and the image-receiving-antenna number N2. A power supply unit 17 is, for example, a commercially available battery, and the power supply unit 17 supplies electrical power to each of the aforementioned internal units.

The changeover switch SW of the external device 2b outputs the radio signals from the receiving antennas A1 to An to the receiving circuit 11 based on the switching instructions from the switching controller SC. Here, the changeover switch SW has a connecting unit CON, which is an antenna switching unit corresponding to each arranging position of the receiving antennas A1 to An and connecting each of the receiving antennas A1 to An.

The connecting unit CON has a detecting function of detecting a connection state of each of the connectors CON1 to CONn. For example, the connecting unit CON has an unconnected antenna detecting unit with respect to the connector CON1, and the connecting unit CON outputs voltage signals, which are detecting signals, to the selection controller C1 when the connector CON1 is connected to the connecting unit CON. The connecting unit CON has a similar unconnected antenna detecting unit with respect to other connectors CON2 to CONn. Therefore, the selection controller C1 can determine whether the connector CON1, hence the receiving antenna A1, is connected to the connecting unit CON or not by detecting presence or absence of the voltage signals. When the connecting unit CON has a similar detecting unit with respect to each of the connectors CON2 to CONn, the selection controller C1 can determine the presence or absence of the connections of each of the receiving antennas A1 to An.

In FIG. 2, the receiving circuit 11, which is a receiving unit, amplifies and modulates the radio signals as described above, and outputs resulting image signals S1 to the signal processing circuit 12 as well as outputs received intensity signals S2 that are receiving electric field intensity of the amplified and modulated radio signals to the sample-and-hold circuit 15. The image data processed at the signal processing circuit 12 are recorded in the memory 13 by the control unit C, as well as the image data are output so as to be displayed by the display unit 14. Signals that are sampled and held by the sample-and-hold circuit 15 are converted to digital signals at the A/D converter 16, and taken into the control unit C. Then, the control unit C selects a receiving antenna that received the largest receiving electric field intensity as a receiving antenna of an image signal period as well as sequentially selects a receiving antenna other than the selected receiving antenna as a receiving antenna of an intensity receiving period. Then, signals S4 that assign the image-receiving-antenna number N2 or the intensity-receiving-antenna number N1 to each of the selected receiving antenna just mentioned are output to the switching controller SC. Here, the selection controller C1 selects only currently connected receiving antennas A1 to An based on signals S6 as the receiving antennas to be switched. Further, the control unit C records the receiving electric field intensity of each of the intensity receiving period and the image receiving period in the memory 13 with the image data, in association with the selected receiving antennas. The recorded receiving electric field intensity of each of the receiving antennas is information for calculating position of the capsule endoscope 3 inside the body cavity when the image data are received.

The switching controller SC has the intensity-receiving-antenna number N1 and the image-receiving-antenna number N2 that are assigned by the selection controller C1. The switching controller SC outputs a signal S5 that indicates instructions for the changeover switch SW to select and connect the receiving antenna from A1 to An that corresponds to the intensity-receiving-antenna number N1 during the intensity receiving period, and to select and connect the receiving antenna from A1 to An that corresponds to the image-receiving-antenna number N2 during the image receiving period. Further, the switching controller SC outputs a signal S3a indicating a sample-and-hold timing of the sample-and-hold circuit 15, a signal S3b indicating an A/D conversion timing of the A/D converter, and a signal S3c indicating a selection controlling timing of the selection controller C1.

Further, the receiving circuit 11 extracts and outputs identification information of the capsule endoscope 3 (hereinafter referred to as "capsule ID") and color adjusting information (white balance data; hereinafter referred to as "WB data") from every received frame. The control unit C has a function as a lock controlling unit, and the control unit C determines whether input capsule ID and the input WB data are identical to previous ones. The control unit C has an internal memory not shown, and the control unit C records the input capsule ID and the WB data into the internal memory as well as monitors the capsule ID and the WB data. When identical capsule ID and identical WB data are repeated input during the predetermined period, the control unit C locks WB data (for example, WB coefficient) on the identical WB data. Then, the control unit C outputs the locked WB data to the signal processing circuit 12 after the locking, and the control unit C outputs the received WB data to the signal processing circuit 12 before the locking. The signal processing circuit 12 having a function as an image processing unit performs image processing on the image signals S1 input from the receiving circuit 11 based on the locked or received WB data just mentioned.

Figure 3:
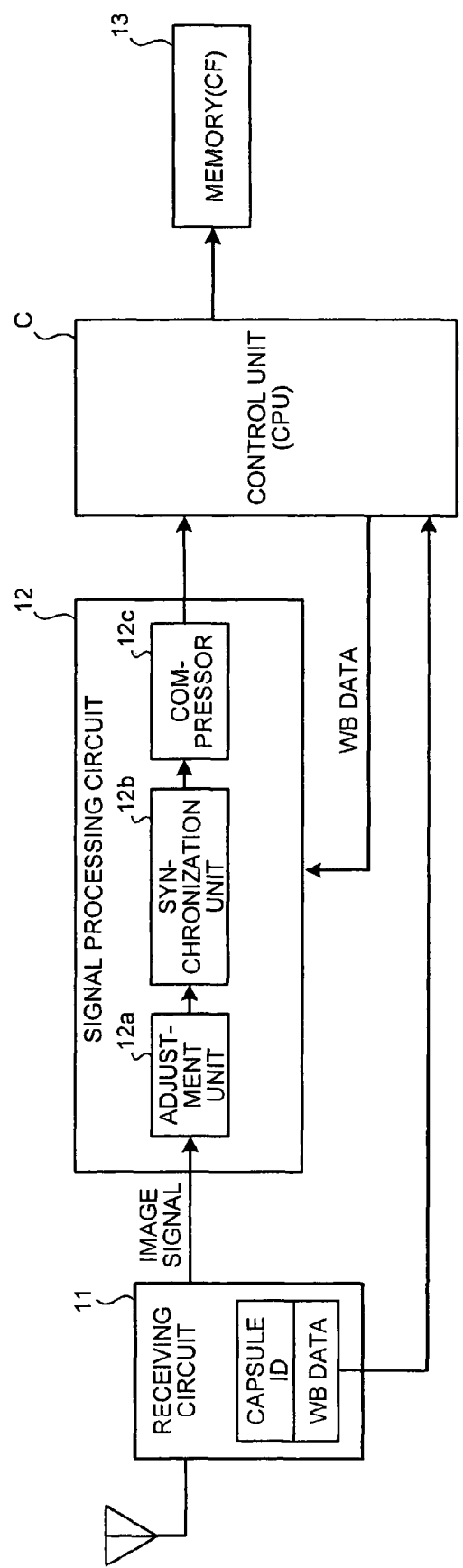
FIG. 3 is a block diagram showing a configuration of a relevant part shown in FIG. 2.

The signal processing circuit 12 has a WB adjustment unit 12a, a synchronization unit 12b, and a compressor 12c as shown in a block diagram of FIG. 3. The WB adjustment unit 12a performs white balance adjustment of the image signals S1 input from the receiving circuit 11. The synchronization unit 12b performs reproduction processing on the image in which the white balance thereof is adjusted. The compressor 12c compresses the reproduced image. More particularly, the WB adjustment unit 12a performs white balance adjustment of the image signals S1 based on the WB data input from the control unit C, and outputs the image signals to the synchronization unit 12b. The synchronization unit 12b performs image reproduction processing in which color information of R, G, and B are acquired for each pixel. Further, the compressor 12c compresses the image-reproduced image data by encoding the image-reproduced image data as according to, for example, JPEG and MPEG, and outputs the resulting data to the control unit C. The control unit C records the compressed image data in the memory 13, which is a recording unit.

Figure 4:
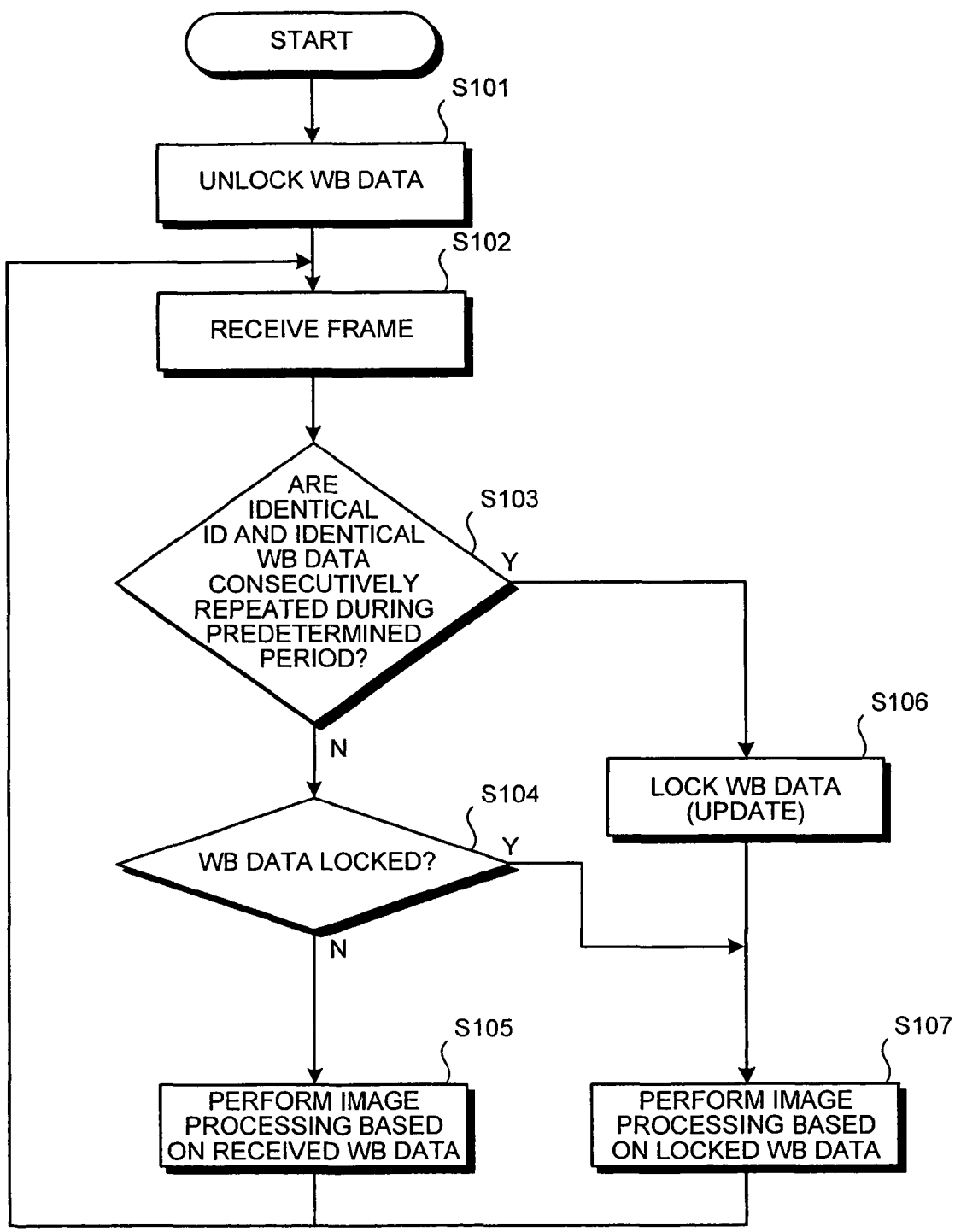
FIG. 4 is a flowchart illustrating an example of an image processing operation at the relevant part shown in FIG. 3.

Next, one example of the image processing operation at a relevant part shown in FIG. 3 is explained with reference to a flowchart of FIG. 4. In FIG. 4, the control unit C unlocks the WB data when initial setting or the like of the system is finished (step S101). Then, the receiving circuit 11 receives the frame including the image signals, extracts the capsule ID and the WB data from the frame, and outputs the extracted capsule ID and the WB data to the control unit C (step S102). The control unit C takes in the capsule ID and the WB data from the receiving circuit 11, and records the capsule ID and the WB data in the internal memory as well as determines whether the identical capsule ID and the identical WB data are repeated consecutively during the predetermined period (step S103).

Here, at first, since the identical capsule ID and the identical WB data are not consecutively repeated during the predetermined period, the control unit C determines whether the WB data is locked or not (step S104).

Here, when the WB data is not locked, the control unit C outputs the received WB data to the signal processing circuit 12, gives the signal processing circuit 12 instructions for performing image processing on the image signals based on the received WB data, and records the image-processed image data in the memory 13 (step S105). On the other hand, when the WB data is locked, the control unit C outputs the locked WB data to the signal processing circuit 12, gives the image processing circuit 12 instructions for performing the image processing on the image signals based on the locked WB data, and records the image-processed image data in the memory 13 (step S107).

Further, when the capsule ID and the WB data are received during the predetermined period and the identical capsule ID and the identical WB data are consecutively repeated during the predetermined period in step S103, the control unit C locks the identical WB data (step S106). Then, the control unit C outputs the locked WB data to the signal processing circuit 12, gives the signal processing circuit 12 instructions for performing the image processing on the image signals based on the locked WB data, and records the image-processed image data in the memory 13 (step S107). In the present embodiment, it is determined whether the identical capsule ID and the identical WB data during the predetermined period are consecutively repeated or not every time the frame is received. The WB data is locked at step S106 every time it is determined that the identical capsule ID and the identical WB data are consecutively repeated, and the WB data is always updated. Therefore, even if the capsule ID and the WB data are changed, the new and changed WB data is locked by the control unit C as a basis of the image processing when the identical capsule ID and the identical WB data are determined to be consecutively repeated in step S103.

As described hereinbefore, in the present embodiment, the identical WB data is locked when the identical capsule ID and the identical WB data are consecutively repeatedly received during the predetermined period. Then, the image processing is performed on the received image signals based on the locked WB data. Consequently, even if the capsule ID and the WB data are temporary changed due to a communication error of the capsule ID and the WB data while receiving the image signals, the invalidation of the image due to the transmission error of the capsule ID and the white balance data transmitted to the receiving apparatus from the capsule endoscope while transmitting the frame including the image signals can be prevented.

In the present embodiment, the WB data is locked when the identical capsule ID and the identical WB data are consecutively repeated during the predetermined period. However, the present invention is not limited thereto. For example, the WB data may be locked when one of the identical capsule ID and the identical WB data is consecutively repeated during the predetermined period. If only the consecutiveness of the identical WB data is determined, the extraction and the outputting of the capsule ID by the receiving circuit 11 become unnecessary.

Further, in the present invention, it is possible to detect how often the identical capsule ID and the identical WB data are received during a predetermined period, and WB data of a group in which the identical capsule ID and the identical WB data are received most often may be locked. Furthermore, in the present embodiment, the image processing is performed based on the received WB data when the WB data is not locked. However, the image processing may be performed by employing a preliminarily determined average WB data.

Figure 5:
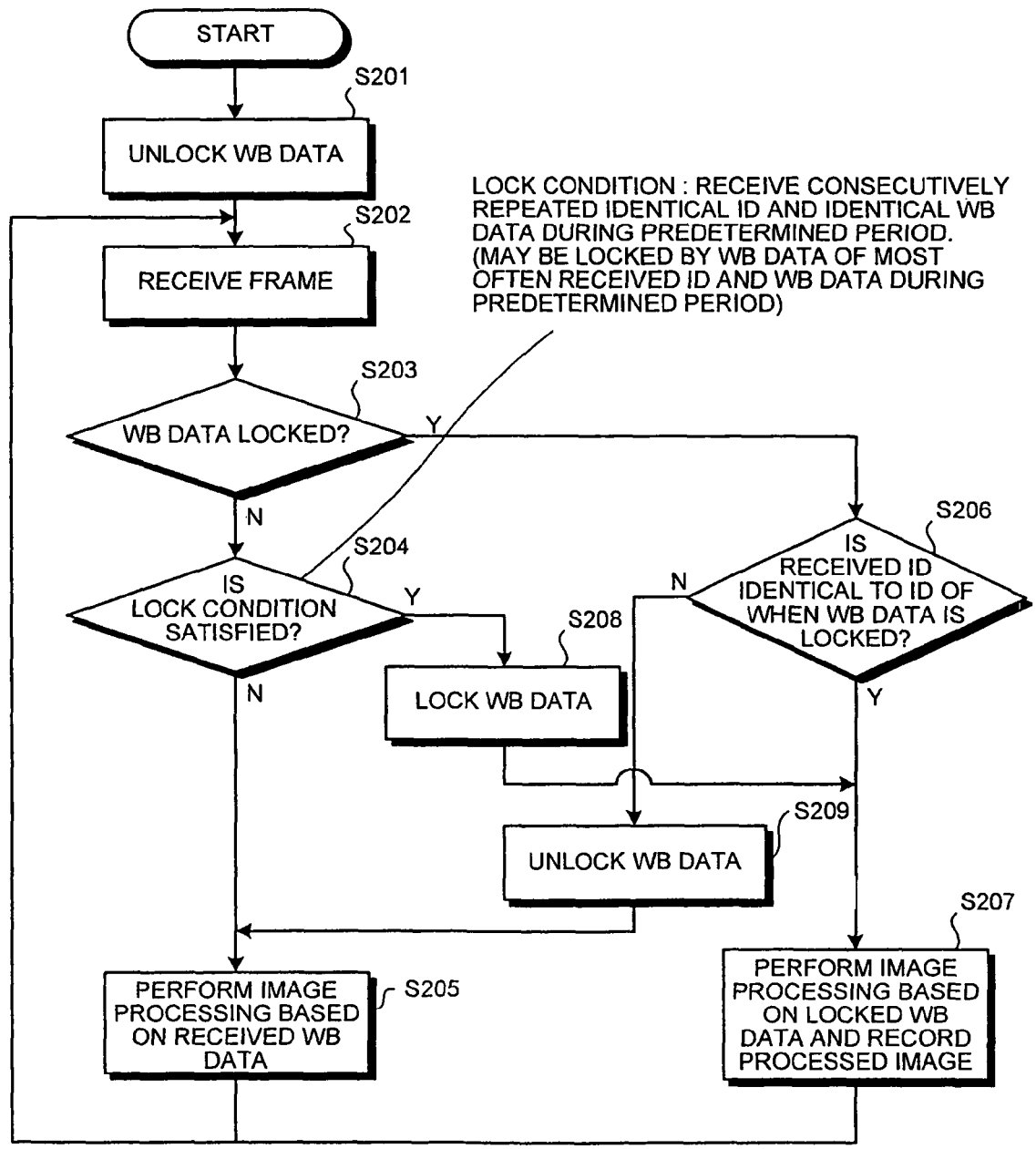
FIG. 5 is a flowchart illustrating another example of the image processing operation at the relevant part shown in FIG. 3.

FIG. 5 is a flowchart illustrating another example of the image processing operation at the relevant part shown in FIG. 3. A block configuration at the relevant part of the receiving apparatus according to the present embodiment is similar to the block configuration of FIG. 3.

The present embodiment differs from the first embodiment since, while having the lock condition shown in the first embodiment (receive consecutively repeating identical capsule ID and identical WB data during the predetermined period), the WB data is unlocked when a received capsule ID differs from a capsule ID of when the WB data is locked, after the WB data is locked. In other words, as similar to the flowchart of FIG. 4 shown in the first embodiment, the receiving circuit 11 extracts the capsule ID and the WB data from the received frame and outputs to the control unit C (step S202) when the control unit C unlocks the WB data (step S201) in FIG. 5. The control unit C determines whether the WB data is locked or not when the capsule ID and WB data are input (step S203).

Here, the WB data is not locked at first, so the control unit C determines whether the input capsule ID and the WB data satisfy the aforementioned lock condition (step S204).

Since the aforementioned lock condition is not yet satisfied, the control unit C outputs the WB data that is included in the received frame to the signal processing circuit 12, and the control unit C commands the signal processing circuit 12 to perform the image processing on the image signals based on the WB data that is included in the received frame (step S205). Further, when the lock condition is satisfied, the WB data that is included in the received frame is locked (step S208). Then, the control unit C outputs the locked WB data to the signal processing circuit 12, commands the signal processing circuit 12 to perform the image processing on the image signals based on the locked WB data, and records the image-processed image data in the memory 13 (step S207).

Further, when the WB data is already locked in step S203, the control unit C determines whether the received capsule ID is identical to the capsule ID of when the WB data is locked or not (step S206).

Here, when the received capsule ID is identical to the capsule ID of when the WB data is locked, the control unit C outputs the locked WB data to the signal processing circuit 12. Then, the control unit C gives the signal processing circuit 12 instructions for performing the image processing on the image signals based on the locked WB data, and records the image-processed image data in the memory 13 (step S207). Further, when the received capsule ID is not identical to the capsule ID of when the WB data is locked, the control unit C unlocks the currently locked WB data (step S209). Then, the control unit C outputs the received WB data to the signal processing circuit 12, gives the signal processing circuit 12 instructions for performing the image processing on the image signals based on the received WB data, and records the image-processed image data in the memory 13 (step S205).

As described hereinbefore, in the present embodiment, the control unit C locks the identical WB data and performs the image processing on the received image signals based on the locked WB data when the identical capsule ID and the identical WB data are consecutively repeatedly received during the predetermined period. Consequently, similarly to the first embodiment, even when the capsule ID and the WB data are changed due to the communication error of the capsule ID and the WB data while receiving the image signals, the invalidation in the image due to the transmission error of the capsule ID and the WB data transmitted from the capsule endoscope to the receiving apparatus while transmitting the frame including the image signals can be prevented. Further, in the present embodiment, before the lock condition is satisfied or when the received capsule ID differs from the capsule ID of when the WB data is locked, the control unit C unlocks the WB data and performs the image processing on the image signals based on the received WB data. Hence, the image processing can be performed on the image signals based on an appropriate WB data when the capsule ID is changed. Consequently, the receiving apparatus according to the present invention can farther flexibly correspond to the transmission error so that the invalidation of the image can be prevented.

In the present embodiment, when the received capsule ID differs from the capsule ID of when the WB data is locked while transmitting the frame with the image signals, the control unit C unlocks the WB data, performs the image processing on the image signals based on the received WB data, and records the image-processed image signals in the memory. However, the present invention is not limited thereto. For example, it is possible to set the receiving apparatus so that when the receiving apparatus receives another capsule ID, receiving apparatus does not record the image data corresponding thereto in the memory. Here, since the image data are not recorded, incorporation of the image data from another capsule endoscope into the image data of the capsule endoscope and mix-up of the image data can be prevented. Further, the present modification may be applied to the first embodiment.

Further, in the present invention, it is possible to apply the configuration shown in the modification of the first embodiment to the second embodiment. In other words, in the second embodiment, it is possible to detect how often the identical capsule ID and the identical WB data are received during the predetermined period, and lock the WB data of a group in which the identical capsule ID and the identical WB data are most often received.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A receiving apparatus that receives an image signal radio transmitted from a movable transmitting apparatus, the receiving apparatus comprising:

a receiving unit that receives identification information on the transmitting apparatus and color adjusting information that are radio transmitted from the transmitting apparatus with the image signal;

a lock controller that locks the color adjusting information when the receiving unit receives at least one of consecutively repeated identical color adjusting information and consecutively repeated identical identification information during a predetermined period or when the receiving unit most often receives at least one of the identical color adjusting information or the identical identification information during the predetermined period; and an image processing unit that performs image processing on the received image signal based on the locked color adjusting information.

2. The receiving apparatus according to claim 1, wherein the lock controller unlocks the color adjusting information after the locking when the identification information received by the receiving unit differ from the identification information at the locking, and the image processing unit performs the image processing on the received image signal based on the received color adjusting information.

3. A receiving apparatus that receives an image signal radio transmitted from a movable transmitting apparatus, the receiving apparatus comprising:

a receiving unit that receives color adjusting information that is radio transmitted from the transmitting apparatus with the image signal;

a lock controller that locks the color adjusting information when the receiving unit receives consecutively repeated identical color adjusting information during a predetermined period or when the receiving unit most often receives identical color adjusting information during the predetermined period; and an image processing unit that performs image processing on the received image signal based on the locked color adjusting information.

* * * * *